United States Patent [19]

Newland

[11] 4,110,261
[45] Aug. 29, 1978

[54] FRAGRANCE-EMITTING ARTICLE HAVING A POLYMER-PETROLEUM WAX COMPOSITION

[75] Inventor: John W. Newland, Hamburg, N.Y.

[73] Assignee: W & F Mfg. Co., Inc., Buffalo, N.Y.

[21] Appl. No.: 779,245

[22] Filed: Mar. 18, 1977

Related U.S. Application Data

[63] Continuation-in-part of Ser. No. 614,493, Sep. 18, 1975, abandoned.

[51] Int. Cl.² .......................... A61K 7/46; C11B 9/00; C10L 5/00
[52] U.S. Cl. ....................................... 252/522; 44/7.5; 424/76; 428/484; 428/905
[58] Field of Search .................. 44/7.5; 431/288, 126; 106/272; 252/522; 424/76, 83; 428/484, 905

[56] References Cited

U.S. PATENT DOCUMENTS

| | | | |
|---|---|---|---|
| 1,701,844 | 2/1929 | Funke | 44/7.5 |
| 2,865,806 | 12/1958 | Bulloff | 424/76 |
| 3,630,697 | 12/1971 | Duling et al. | 44/7.5 |
| 3,771,445 | 11/1973 | Campbell et al. | 44/7.5 X |
| 3,843,312 | 10/1974 | Easterday | 431/288 |
| 3,925,029 | 12/1975 | Wilson | 44/7.5 |
| 4,051,159 | 9/1977 | Tsoucalas et al. | 252/522 X |

*Primary Examiner*—Carl Dees
*Attorney, Agent, or Firm*—Sommer & Sommer

[57] ABSTRACT

A high level fragrance-emitting article having a polymer-petroleum wax composition possessing the durable physical properties of rigidity, gloss and surface hardness.

2 Claims, No Drawings

FRAGRANCE-EMITTING ARTICLE HAVING A POLYMER-PETROLEUM WAX COMPOSITION

This is a continuation-in-part of application Ser. No. 614,493 filed Sept. 18, 1975 and now abandoned.

This invention relates to the field of thermoplastic materials, and more particularly to an improved thermoplastic material which has desirable physical properties rendering it suitable for formation into fragrance-emitting decorative articles such as figurines for placement in a room to mask unpleasant odors or to supply a pleasant odor. For generic identification, the inventive composition is identified as a polymer-petroleum wax composition.

The inventive composition is an improvement over two prior art types of compositions used for similar purposes. One prior art type is designated a paraffin wax composition which when formed into a figurine had a dull, glossless surface and was relatively soft. The other prior art type is designated a polyamide resin composition which, while having desired and increased gloss and transparency characteristics, was subject with age to becoming tacky to touch and provided a surface more difficult to keep clean.

An article embodying the present invention possesses an adequate capacity, in fact, a high level capacity, to emit a fragrance, without the need for burning.

Fragrance-emitting candles are known having a wax-like composition containing a relatively small amount of fragrance ingredient. While such candles before ignition have a quiescent fragrance-emitting capability, the full capacity is not realized until ignited to emit more fragrance. When ignited the accentuated fragrance emanates from a molten puddle of composition formed around the base of the candle's wick. Since ignition is relied upon to develop the desired higher level of fragrance emission, the composition usually contains a relatively small amount of fragrance ingredient. This preserves acceptable physical properties of the candle.

It would seem logical that if one wanted an article to emit more fragrance, without igniting it as is done with a candle, simply more fragrance ingredient could be added to the composition. This is where the problem is created, solved by the present invention. Addition of more fragrance ingredient destroys or deleteriously affects some desired physical characteristics of the prior art compositions.

If, for example, the prior art paraffin wax type composition, mentioned hereinabove, is used with an increased amount of fragrance ingredient, the shaped article has a dull, glossless surface and is relatively soft.

Also, if a polyamide resin composition, another prior art type mentioned hereinabove, is utilized with an increased amount of fragrance ingredient, the article formed from such composition initially has a desired gloss but is not durable and becomes tacky with age, rendering it undesirable in feel and more difficult to keep its surface free from dust and dirt.

Compared to both prior art compositions, the polymer-petroleum wax composition of the present invention has a decided advantage in being able to contain more perfume fragrance and has better fragrance emission properties. Compared to the prior art polyamide compositive, the inventive polymer-petroleum wax composition suffers less loss and degradation of the perfume fragrance during processing of the composition due to lower processing temperatures being used.

The primary objective of the present invention is to provide a durable decorative article, easily manufactured, possessing the desirable physical characteristics of rigidity, gloss, surface hardness and relatively high fragrance emissivity, and overcoming the forementioned disadvantages of the prior art compositions.

The petroleum wax ingredient of the inventive composition is present in principal amount by weight. As used herein, a petroleum wax suitable for use as an ingredient in the inventive composition is intended to be one, or a mixture of one or more, of the waxes classified on page 216 of the book entitled The Chemistry and Technology of Waxes, by Allan H. Warth, published in 1947 by Reinhold Publications, New York City. These would include, for example, refined paraffin waxes, semi-refined paraffin waxes, and micro-crystalline waxes.

The polymer ingredient of the inventive composition is present in an amount by weight less than the petroleum wax ingredient, and from 3% to 25% by weight of the composition. This polymer ingredient must be one, or a mixture of one or more, of the polymers selected from the group consisting of ethylene vinyl acetate, ethylene vinyl acetate acid terpolymer, ethylene ethyl acrylate, ethylene isobutyl acrylate, polyethylene and polypropylene.

It is essential in the practice of the present invention that each of the aforementioned six operative members of the polymer group have a weight average molecular weight of below about 10,000. This low molecular weight characteristic minimizes blending problems of the polymer with other ingredients, and also keeps the viscosity of the composition low during formation of the article as by the simple and inexpensive method of flush molding, which is the preferred technique and described in detail later herein.

Examples of polymers that can be used in the practice of the present invention, by trade name and producer, include the following:

| | | |
|---|---|---|
| Ethylene vinyl acetate | Elvax (various grades) | DuPont |
| Ethylene vinyl acetate acid terpolymer | Elvax (various grades) | " |
| Ethylene vinyl acetate | A/C400 (various grades) | Allied Chemical Plastics Div. |
| Polyethylene | A/C Polyethylenes | " |
| Ethylene ethyl acrylate | Zetafax | Dow Chemical Company |
| Ethylene isobutyl acrylate | " | " |
| Ethylene vinyl acetate | " | " |
| Polyethylene | Epolene | Eastman Chemicals |
| Ethylene vinyl acetate copolymer | Ultrathene (various grades) | U.S.I. Chemical |
| Polyethylenes | Petrothene (various grades) | " |
| Polypropylenes | " | " |

The third essential part of the inventive composition is a perfume fragrance ingredient, which is present in amount to make up substantially the balance of 100% by weight of the composition. The perfume fragrances employed in the practice of the present invention are those known to persons skilled in this art, presently available commercially and the same as those heretofore used in connection with the prior art compositions.

If a composition of the present invention is desired to be colored, a suitable dye or coloring material of the present commercially available ones, and which have been used in the prior art compositions, also known to persons skilled in the art, may be employed to achieve the color desired.

Minor amounts of other non-essential but desirable ingredients which contribute a stabilizing effect on the article formed from the inventive composition, may be included, such as an anti-oxidant or ultraviolet light stabilizer.

The following Example is a preferred formulation of the inventive composition which has been found particularly useful for the molded shell of perfumed figurines.

EXAMPLE 74.959% refined paraffin wax having a 143°–145° F. melting point
10.0% Elvax 250 (ethylene vinyl acetate)
15.0% perfume fragrance
0.001% BHT (butylated hydroxytoluene)
0.010% UV531 (ultraviolet stabilizer)
0.010% UV5411 (ultraviolet stabilizer)
0.020% $TiO_2$ (titanium dioxide)

To blend this formation, the Elvax 250, which has a weight average molecular weight below 10,000, is added to the paraffin wax along with the BHT and heated to a temperature of 240°–250° F. and put into solution using a cowles dissolver. As soon as the mixture is homogenous the temperature is decreased to 180° F. and the perfume fragrance, which was previously mixed with the $TiO_2$, UV521 and UV5411, is added to the homogenized polymer-paraffin wax blend and the temperature is maintained at approximately 170° F.

The BHT acts as an anti-oxidant. The UV531 and UV5411 are ultraviolet light stabilizers and do not function in any other capacity. The $TiO_2$ is a whitener and filler and functions only in that capacity. Other colorants may be substituted as desired. While the composition has been described as prepared from two separately prepared mixtures, this is merely preferred and not critical. The $TiO_2$, UV531 and UV5411 may be combined with Elvax 250 and paraffin wax prior to blending, as desired.

The resulting composition is then utilized to mold a figurine according to a preferred flush molding technique now to be described. According to this technique, a mold of the described configuration having a filling opening is prepared by immersion in a solution of water and surfactant, an emulsion of silicone oil in water such as Dow Corning 36, at 105° F. and then blown free of water droplets.

The polymer-paraffin wax composition of the above Example at 170°–180° F. is then poured through the mold opening into the mold cavity which is filled. The fill begins to harden from its outside surface, in contact with the wall of the mold cavity, progressively inwardly toward the center of the cavity, to form a shell surrounding a still fluid body. The fill is left to dwell for a time period depending upon the weight of the shell or shell thickness desired to be formed within the mold. The mold is then inverted and the unsolidified material within the solidified shell is poured out. The mold is then returned to an upright position with the mold opening at the top, and the excess of solidified fill at such opening is cut off.

Preferably the hollow shell so molded is then filled with core wax that has been aerated and is at a temperature approximately 5° F. below its melting point, a preferred formulation of which will include:

79.999% refined paraffin wax having a 143°–145° F. melting point
15.000% microcrystalline wax having a 170°–180° F. melting point
5.000% A/C400 (an ethylene vinyl acetate copolymer)
0.001% BHT (butylated hydroxytoluene) or BHA (butylated hydroxyanisole)

The A/C400, having a weight average molecular weight of about 2000, is added to the refined paraffin and micro-crystalline wax with the BHT or BHA, both anti-oxidants, at approximately 190°–200° F. with stirring or agitation. As soon as the mixture is homogenous the temperature is decreased to 160° F. and processed through a foaming device, known as a votator, and then poured into the molded shell until the shell is filled. This core wax formulation contains no perfume fragrance.

The mold, with its aerated core wax filled shell, is then placed in cooling water at approximately 90° F. and allowed to cool for a period of time sufficiently long to allow removal of the excess fill wax by cutting, and removal of the molded article at a temperature low enough to be stable. The mold is then removed from the cooling water and the product or molded article is removed from the mold. The product is then placed on a conveyor belt which carries it through a cooling tunnel in which an air temperature of about 60° F. is maintained.

In this manner, an article can be produced comprising a fragrance-emitting, dense, outer shell having the desired physical properties, surrounding a body of lightweight, aerated, core wax unladen with a perfume fragrance ingredient.

Alternatively, while the mold may be completely filled with the fragrance containing polymer-petroleum wax composition, this would result in a molded article which is needlessly heavy and containing the fragrance ingredient in the central portion of the article where it cannot be effectively emitted. Accordingly, it is preferred that the article construction have a fragrance-laden, non-cellular, outer shell filled with a perfume-unladen, cellular, core. Any suitable core wax formulation other than the one given, as an example, may be used.

Perfume emission evaluation of the inventive polymer-petroleum wax composition indicates that the perfume is emitted at a substantially higher rate than from the prior art compositions.

Further, the inventive polymer-petroleum wax composition can be processed at a temperature 50°–60° F. lower than the prior art polyamide composition, thus decreasing the loss of perfume, the possibility of material degradation due to oxidation including perfume, petroleum wax and dyes. In this regard, the processing temperature is approximately the same as the prior art paraffin wax composition.

Still further, the initial gloss and gloss retention properties of the inventive polymer-petroleum wax composition are superior to those of the prior art paraffin wax composition, and at least equal to those of the prior art polyamide composition.

Also, the penetration resistance and hardness of the inventive polymer-petroleum wax composition are greater than those of the two prior art compositions.

Additional desirable properties and advantages of the inventive polymer-petroleum wax composition, rendering it superior to the aforementioned two prior art compositions, include greater toughness and durability.

These properties permit easier handling in the manufacturing process, require less care in packaging and shipping, and also provide a more satisfactory material for customer usage. Another advantageous property is the higher softening temperature which improves heat stability in storage, shipping and usage by the customer. Still another advantageous property is its smooth surface which may be readily cleaned.

In the case of a molded article having a shell made of the inventive polymer-petroleum wax composition, the strength of such shell is substantially higher than for a similar shell made of either of the aforementioned two prior art compositions.

While the inventive polymer-petroleum wax composition may be manufactured into various shapes and sizes using processes, besides the flush molding technique described, such as rotational molding, injection molding and compression molding, these require special machines. Moreover, injection and compression molding would produce only a solid article and would not permit a shell to be formed. The flush molding technique can be used to form successively both the non-cellular outer shell and the cellular core, and is the easiest, simplest and most economical method of production.

While examples of the best modes of carrying out the invention have been described, the scope of the invention is not to be limited thereto but is to be determined by the appended claims.

What is claimed is:

1. A fragrance-emitting article having a composition, suitable for flush molding, comprising essentially about 75% by weight of petroleum wax; about 10% by weight of polymer selected from the group which consists of ethylene vinyl acetate, ethylene vinyl acetate acid terpolymer, ethylene ethyl acrylate, ethylene isobutyl acrylate, polyethylene and polypropylene, each of such members of said group having a weight average molecular weight below about 10,000; and about 15% by weight of a perfume fragrance.

2. A fragrance-emitting article according to claim 1 which includes an outer shell having said composition, and a body of aerated core wax unladen with perfume fragrance filling said shell.

* * * * *